(12) United States Patent
Jones

(10) Patent No.: US 11,974,725 B2
(45) Date of Patent: May 7, 2024

(54) OPTICAL SYSTEM HAVING TAPERED LIGHT TRANSMISSION ELEMENT

(71) Applicant: Fraen Corporation, Reading, MA (US)

(72) Inventor: Carlton S. Jones, Boxford, MA (US)

(73) Assignee: Fraen Corporation, Reading, MA (US)

(*) Notice: Subject to any disclaimer, the term of this patent is extended or adjusted under 35 U.S.C. 154(b) by 186 days.

(21) Appl. No.: 16/998,565

(22) Filed: Aug. 20, 2020

(65) Prior Publication Data

US 2021/0055538 A1    Feb. 25, 2021

Related U.S. Application Data

(60) Provisional application No. 62/890,270, filed on Aug. 22, 2019.

(51) Int. Cl.
| | |
|---|---|
| *A61B 1/07* | (2006.01) |
| *A61B 1/00* | (2006.01) |
| *G02B 23/24* | (2006.01) |

(52) U.S. Cl.
CPC ............ *A61B 1/07* (2013.01); *A61B 1/00097* (2022.02); *G02B 23/2469* (2013.01)

(58) Field of Classification Search
CPC ... A61B 1/00096; A61B 1/00126; A61B 1/07; G02B 6/4206; G02B 6/4214; G02B 6/4298; G02B 23/2461; G02B 23/2469
See application file for complete search history.

(56) References Cited

U.S. PATENT DOCUMENTS

| | | | | |
|---|---|---|---|---|
| 3,437,804 A | * | 4/1969 | Schaefer | G02B 6/4298 |
| | | | | 353/55 |
| 4,576,435 A | * | 3/1986 | Nishioka | G02B 6/4298 |
| | | | | 607/93 |
| 5,491,765 A | * | 2/1996 | Matsumoto | G02B 6/4298 |
| | | | | 359/708 |

(Continued)

FOREIGN PATENT DOCUMENTS

| | | | |
|---|---|---|---|
| EP | 0821254 A1 | * | 1/1998 |
| JP | 2015103303 A | | 6/2015 |

(Continued)

OTHER PUBLICATIONS

International Search Report and Written Opinion, PCT/US2020/047197, dated Nov. 4, 2020, 15 pages.

*Primary Examiner* — John P Leubecker
*Assistant Examiner* — Jae Woo
(74) *Attorney, Agent, or Firm* — Potomac Law Group, PLLC; Reza Mollaaghababa; Reza Sadr

(57) ABSTRACT

In one aspect, an optical system is disclosed, which comprises a lens having an input surface for receiving light from at least one light source and an output surface through which the light exits the lens, said lens further comprising a peripheral surface extending between said input surface and said output surface and configured to direct, via total internal reflection, at least a portion of the light incident thereon through said output surface to an output focal point. The optical system can further include a tapered light pipe optically coupled to the lens and a light guide (e.g., one or more optical fibers) that is optically coupled to the tapered light pipe. The lens directs the received light to an output focal point that is disposed within the tapered light pipe.

23 Claims, 5 Drawing Sheets

(56) References Cited

U.S. PATENT DOCUMENTS

| | | | | |
|---|---|---|---|---|
| 2006/0158896 A1* | 7/2006 | Krupa | ................ | G02B 19/0028 |
| | | | | 362/555 |
| 2010/0330523 A1 | 12/2010 | Kert | | |
| 2014/0112016 A1* | 4/2014 | Hatanaka | ............. | A61B 1/0684 |
| | | | | 362/574 |
| 2017/0123199 A1* | 5/2017 | Jones | ................... | G02B 6/0008 |

FOREIGN PATENT DOCUMENTS

| | | | |
|---|---|---|---|
| WO | 2007078941 | A1 | 7/2007 |
| WO | 2011004241 | A1 | 1/2011 |

* cited by examiner

OPTICAL SYSTEM HAVING TAPERED LIGHT TRANSMISSION ELEMENT

RELATED APPLICATION

The present application claims priority to a Provisional Application No. 62/890,270 filed on Aug. 22, 2019, and which is herein incorporated by reference in its entirety.

BACKGROUND

The present teachings are directed to an optical system and more particularly to an optical system that can be employed in medical instruments, such as an endoscope.

Optical systems are employed in a variety of medical instruments to illuminate a target region. Many such optical instruments employ optical fibers to transmit light from a light source to a target area to be illuminated. As shown in FIG. 1, one standard way of coupling light from a light source 1 into an optical fiber is to employ a lens 3 having an elliptically-shaped total-internal-reflection (TIR) peripheral surface, which is optically coupled at one focal point ($f_{in}$) to a surface of a light source and which directs the light to another focal point ($f_{out}$) near the input surface of the optical fiber 2.

Many endoscopes, however, include an integral tapered glass optical element 4 shown in FIG. 2, which attempts to funnel the light from standard endoscope light sources (typically xenon or halogen bulbs) into the fiber 2. The light rays that encounter the peripheral surface of the tapered glass optical element reflect at angles that typically result in many of the rays escaping from the system (e.g., rays A, B, and C) via refraction.

Accordingly, there is a need for optical systems that can provide enhanced coupling for light from a light source into an optical fiber, and particularly optical systems that can be incorporated in medical instruments, such as endoscopes.

SUMMARY

In one aspect, an optical system is disclosed, which comprises a lens having an input surface for receiving light from at least one light source and an output surface through which the light exits the lens, said lens further comprising a peripheral surface extending between said input surface and said output surface and configured to direct, via total internal reflection, at least a portion of the light incident thereon through the output surface to an output focal point. The optical system can further include a tapered light pipe having an input surface that is optically coupled to said output surface of the lens for receiving at least a portion of the light exiting the lens and an output surface through which at least a portion of the received light exits the light pipe, said light pipe further comprising a lateral surface extending between said input and said output surface, wherein said light pipe exhibits a decreasing cross sectional area from said input surface to said output surface thereof. A light guide is optically coupled to the tapered light pipe to receive at least a portion of the light exiting the output surface of the light pipe, wherein said output focal point of the lens is positioned within said tapered light pipe.

In some embodiments, the output focal point is positioned within the tapered light pipe at a location selected so as to inhibit light diverging from the output focal point from exiting the tapered light pipe via said peripheral surface thereof.

In some embodiments, the output focal point is positioned along an optical axis of the tapered light pipe. Further, in some embodiments, the location of the output focal point is closer to the output surface of the tapered light pipe than its input surface.

By way of example, in some embodiments, the output focal point is positioned at a location within the tapered light pipe such that at least about 80% of light diverging from the output focal point exits the tapered light pipe without striking the peripheral surface thereof.

In some embodiments, the output focal point is positioned at a location within the tapered light pipe such that light diverging from said output focal point exhibits a divergence angle commensurate with a numerical aperture of said light guide.

In some embodiments, the tapered light pipe exhibits a draft angle in a range of about 1 to about 20 degrees.

In some embodiments, the input surface of the lens includes a cavity of receiving the light emitted by the light source. In some embodiments, such a cavity can be configured to receive at least a portion of the light source.

In some embodiments, at least a portion of the peripheral surface of the lens has an ellipsoidal shape characterized by an input focal point positioned in proximity of its input surface and an output focal point that is positioned within the tapered light pipe. In some embodiments, a light-emitting surface of the light source (e.g., a light-emitting surface of an LED or a halogen bulb) is positioned at or in proximity of the input focal point.

In some embodiments, a maximum distance ($x_{max}$) of the output focal point relative to the output surface of the tapered light pipe is given by the following relation:

$$x_{max} = \frac{R_{out}}{\tan(\alpha/2)}$$

where, $R_{out}$ denotes the radius of said output surface of the light pipe, and $\alpha$ denotes divergence angle of the light propagating beyond said output focal point.

In a related aspect, an endoscope is disclosed, which comprises an optical system for receiving light from at least one light source and for directing the light to a body portion for illumination thereof. The optical system can include a lens having an input surface for receiving light from at least one light source and an output surface through which the light exits the lens, said lens further comprising a peripheral surface extending between the input surface and the output surface and configured to direct, via total internal reflection, at least a portion of the light incident thereon through said output surface to an output focal point. The optical system further includes a tapered light pipe having an input surface that is optically coupled to the output surface of the lens for receiving at least a portion of the light exiting the lens and an output surface through which at least a portion of the received light exits the light pipe, said light pipe further comprising a lateral surface extending between said input and said output surface, wherein said light pipe exhibits a decreasing cross sectional area from said input surface to said output surface thereof. A light guide is optically coupled to the tapered light pipe to receive at least a portion of the light exiting the output surface of the light pipe, where the output focal point of the lens is positioned within said tapered light pipe.

In some embodiments of the endoscope, the output focal point is positioned within said tapered light pipe at a location selected so as to inhibit at least about 80% of the light diverging from said output focal point from exiting the tapered light pipe via said peripheral surface thereof. By way of example, the output focal point can be positioned along an optical axis of the tapered light pipe, e.g., at a location that is closer to the output surface of the tapered light pipe than its input surface. In some such embodiments, the output focal point can be positioned at a location within the tapered light pipe such that at least about 80% (e.g., at least about 90% or 100%) of light diverging from the output focal point exits the tapered light pipe without striking the peripheral surface thereof. In some such embodiments, the output focal point is positioned at a location within said tapered light pipe such that light diverging from said output focal point exhibits a divergence angle commensurate with a numerical aperture of said light guide. Further, in some embodiments, the taper of the tapered light pipe can be characterized by a draft angle in a range of about 1 degree to about 20 degrees.

Further understanding of various aspects of the present teachings can be obtained by reference to the following detailed description in conjunction with the associated drawings, which are described briefly below.

DETAILED DESCRIPTION

The present teachings are generally directed to an optical system that allows for efficient coupling of light emitted by a light source, such as an endoscope, for illuminating a target region of interest. Various terms are used herein in accordance with their ordinary meanings in the art. The term "numerical aperture," as used herein, refers to a dimensionless number that characterizes the range of angles over which the system can accept or emit light.

The term "about" as used herein is intended to indicate a maximum variation (e.g., of a numerical value) of 5%.

Figure 1:
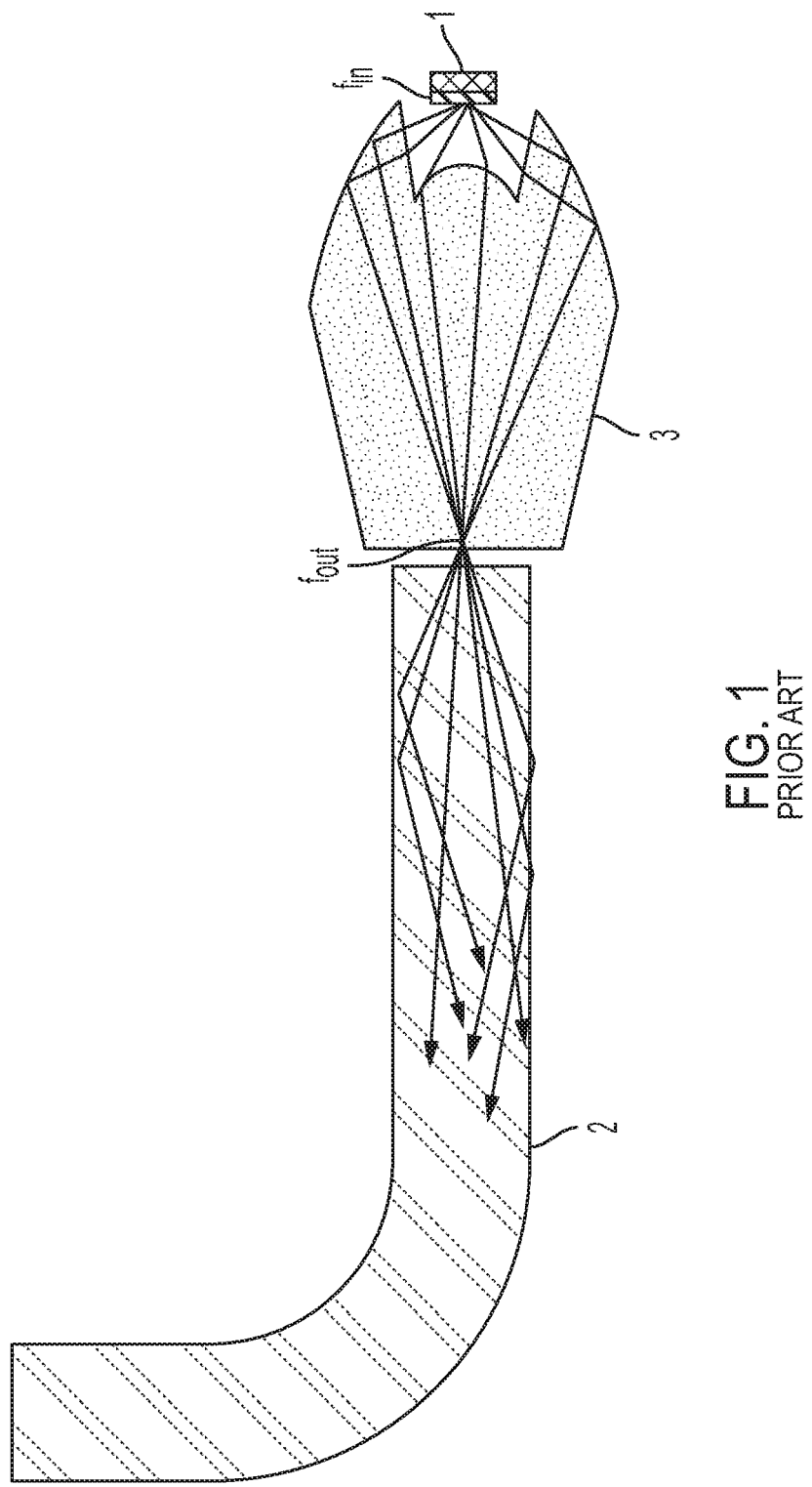
FIG. 1 schematically depicts a prior art system for coupling light from a light source into a light guide (e.g., an optical fiber), FIG. 2 schematically depicts an optical system for use in an endoscope for transmitting light from a light source to a target region, FIGS. 3A and 3B schematically depict an optical system according to an embodiment of the present teachings, and FIG. 4 schematically depicts an endoscope in which an optical system according to the present teachings is incorporated.
Figure 2:
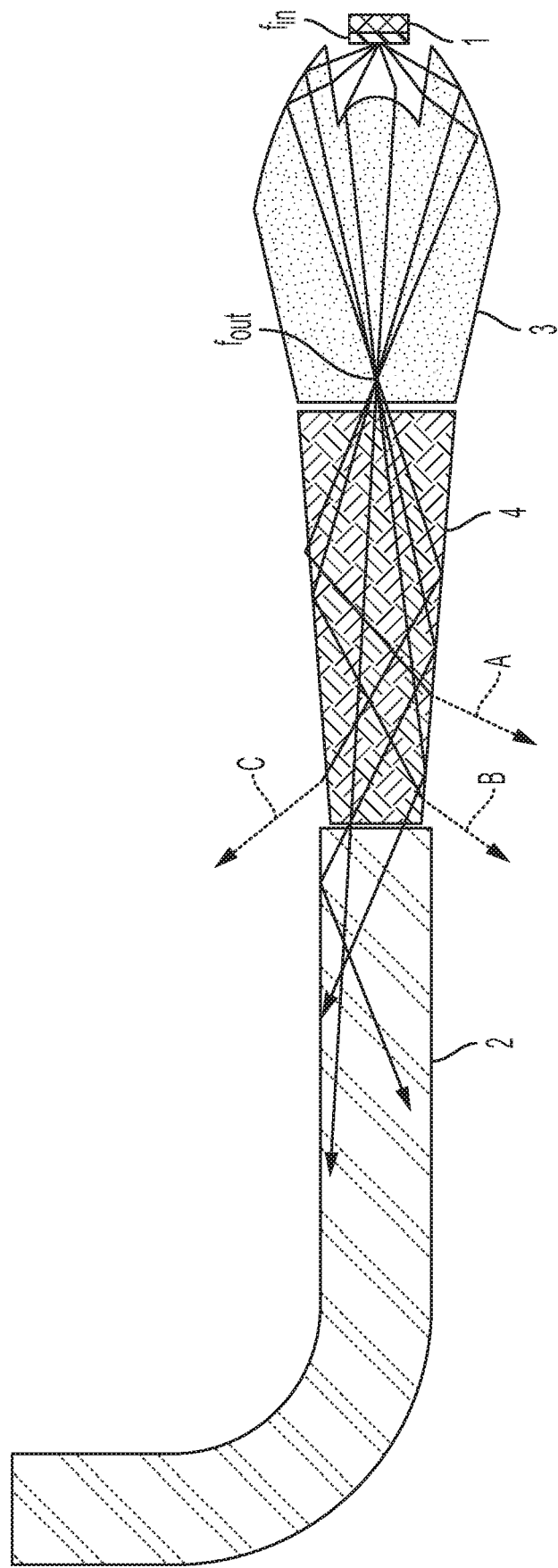
Figure 3A:
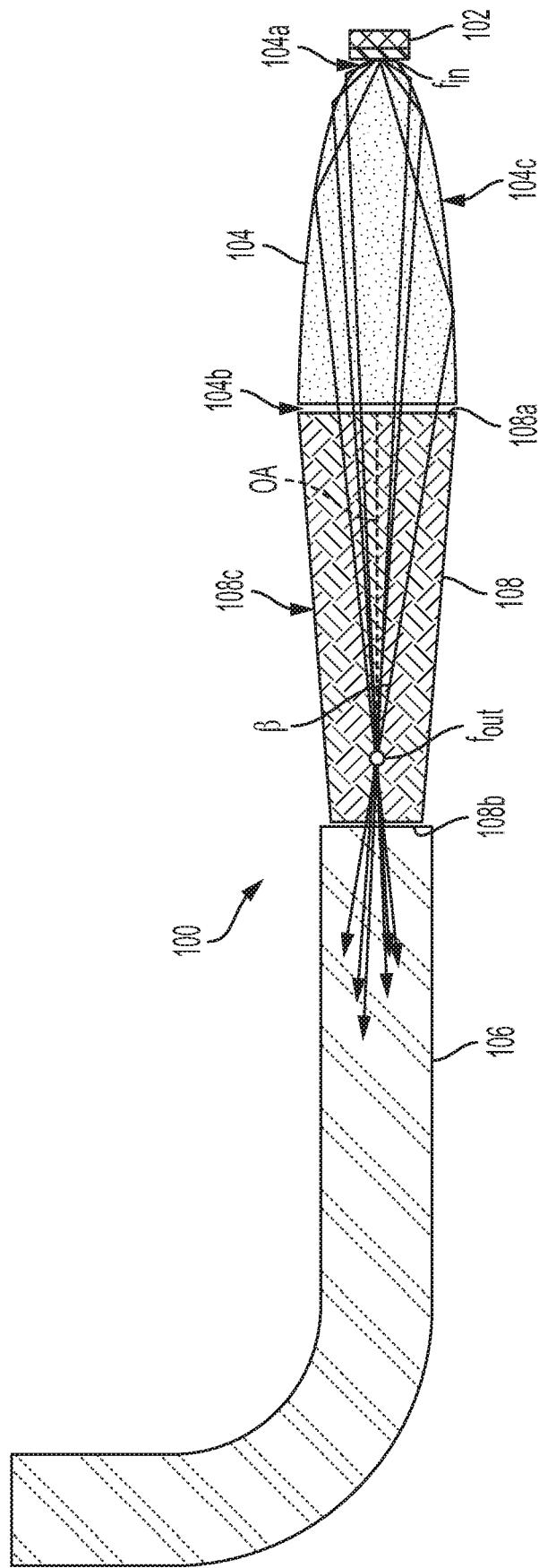
Figure 3B:
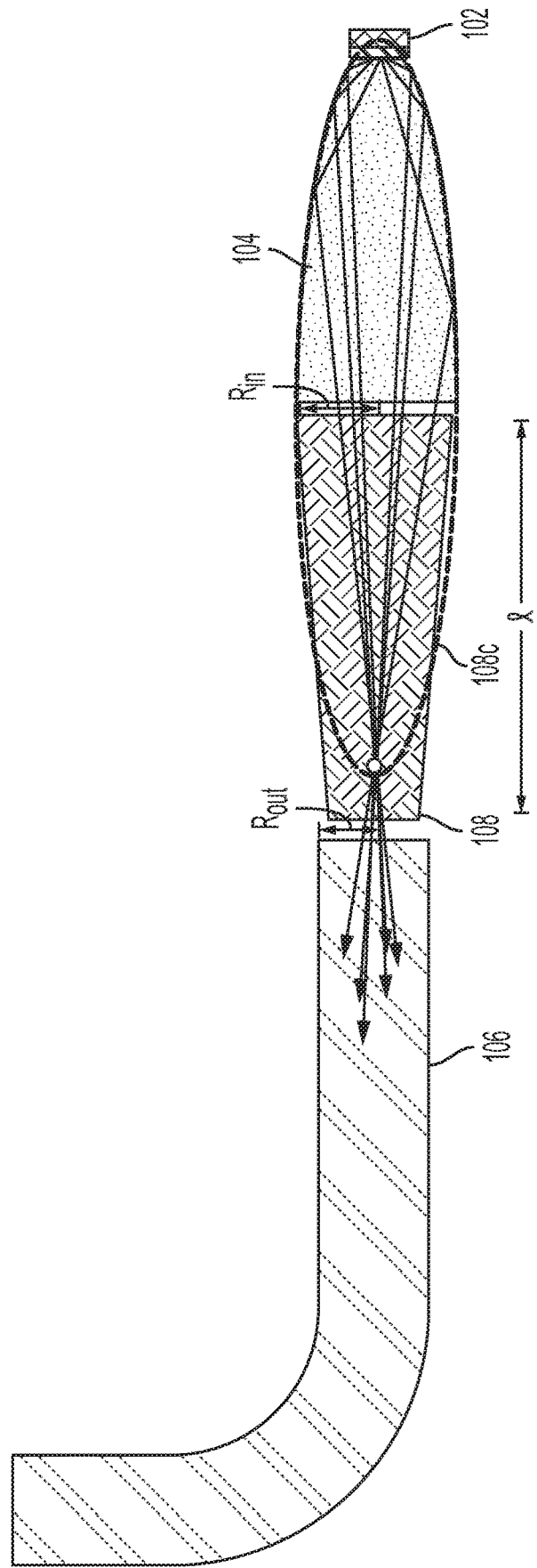

With reference to FIGS. 3A and 3B, an optical system 100 according to an embodiment includes a light source 102, which is optically coupled to a lens 104 to deliver light thereto. A variety of light sources can be employed in the practice of the present teachings. By way of example, in some embodiments, the light source can be a light-emitting diode (LED or a halogen bulb). In some embodiments, the light source 102 generates light in the visible portion of the electromagnetic spectrum, e.g., in a wavelength region between about 450 nm to about 700 nm, though in other embodiments a light source generating light having other wavelengths can also be employed.

The lens 104 includes an input surface 104a that is optically coupled to the light source 102 to receive light therefrom and an output surface 104b through which the received light, or at least a portion thereof, exits the lens. A peripheral surface 104c extends between the input surface 104a and the output surface 104b. In this embodiment, the peripheral surface 104c is in the form of an ellipsoid (i.e., a three-dimensional shape whose plane sections are ellipses) having two focal points $f_{in}$ and $f_{out}$. In this embodiment, the light source 102 is positioned at or in proximity of the focal point $f_{in}$ (which is herein also referred to as "input focal point") and the focal point $f_{out}$ (which is herein also referred to as "output focal point") is external to the lens 104.

The optical system 100 further includes a light guide 106 and a tapered light pipe 108 that is disposed between the lens 104 and the light guide 106. The tapered light pipe 108 has an input surface 108a for receiving light from the lens and an output surface 108b, which is optically coupled to the light guide 106 such that the light exiting the output surface 108b enters the light guide 106. The tapered light pipe 108 exhibits a decreasing cross-sectional area from its input surface 108a to its output surface 108b. More specifically, in this embodiment, the tapered light pipe 108 has substantially circular input and output surfaces, where radius (Rin) of the input surface of the light pipe is less than a respective radius (Rout) of its output surface. A peripheral surface 108c extends between the input surface 108a and the output surface 108b. The taper of the light pipe 108 can be characterized by a draft angle, which can be, for example, in a range of about 1 degree to about 20 degrees.

In this embodiment, the lens 104 as well as the position of the tapered light pipe 108 relative to the lens 104 are configured such that the output focal point $f_{out}$ is located within the tapered light pipe 108. More specifically, in this embodiment, the output focal point $f_{out}$ is positioned along an optical axis (OA) of the light pipe at a location that is closer to the light pipe's output surface 108b than its input surface 108a.

As shown in FIG. 3A, the light rays entering the light pipe 108 converge onto the output focal point ($f_{out}$) with a convergence angle ($\beta$) and then diverge as they propagate beyond the output focal point ($f_{out}$) toward the output surface of the light pipe (with the divergence angle being equal to the convergence angle). In some embodiments, the lens 104 is configured such that the divergence angle of the light rays propagating beyond the output focal point $f_{out}$ is substantially equal to a numerical aperture of the light guide 106. This allows efficient coupling of the light exiting the tapered light pipe 108 into the light guide 106.

In some embodiments, the maximum distance ($x_{max}$) of the output focal point $f_{out}$ relative to the output surface 108a of the tapered light pipe can be given by the following relation:

$$x_{max} = \frac{R_{out}}{\tan(\beta/2)}$$

wherein,
$R_{out}$ denotes the radius of the output surface of the light pipe, and
$\beta$ denotes divergence angle of the light propagating beyond the output focal point.

The positioning of the output focal point $f_{out}$ within the tapered light pipe as discussed herein ensures that the light entering the light pipe will not exit the light pipe via its peripheral surface, thus allowing an efficient coupling of such light into the light guide 106.

The lens 104, the light pipe 108, and the light guide 106 can be formed of a variety of suitable materials. By way of example, in some embodiments, the lens 104 can be formed of a polymeric material, such as PMMA (polymethyl methacrylate) or PC (poly carbonate). Alternatively, the lens 104 can be formed of glass to allow its coupling to high power light sources (e.g., high power LEDs). In this embodiment, the tapered light pipe 108 is formed of glass, though in other embodiments it can be formed of a suitable polymeric material, such as those discussed above. Further, in this embodiment, the light guide is in the form of an optical fiber (or a bundle of optical fibers), which can provide flexibility in channeling the light introduced into the light guide to a target region.

Figure 4:
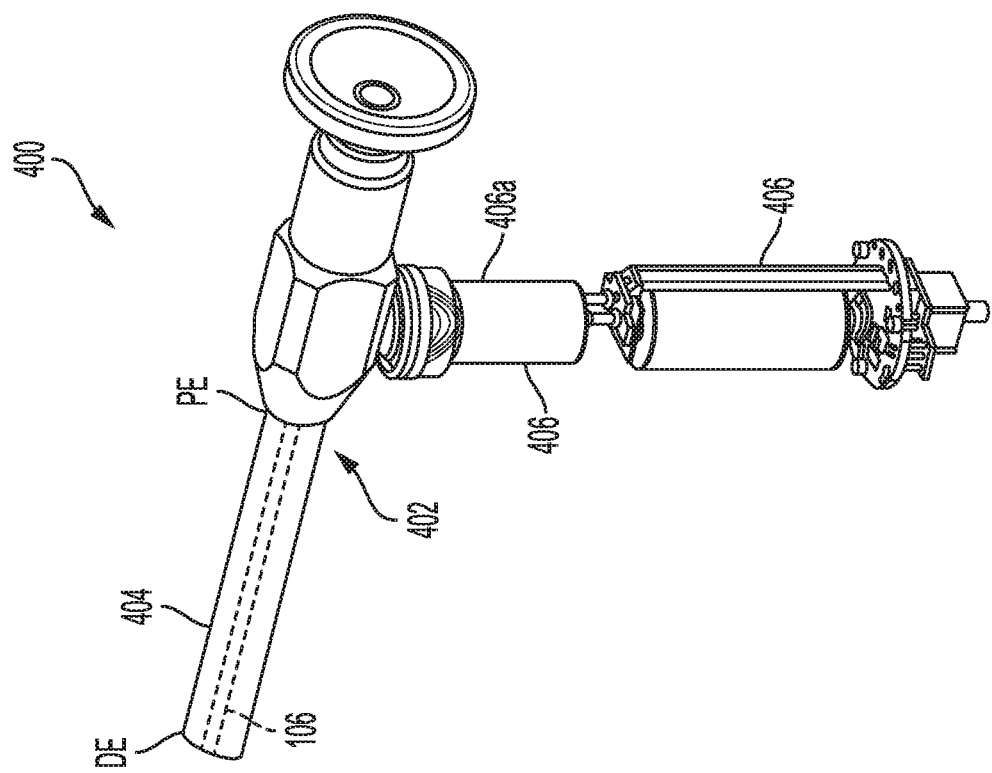

An optical system according to the present teachings can find a variety of applications. By way of example, such an optical system can be incorporated in an endoscope as an illumination source. For example, FIG. 4 schematically depicts an endoscope 400 having an endoscope body 402 including a flexible elongated element 404 that extends from a proximal end (PE) to a distal end (DE). The elongated element is configured for insertion into a patient. The exemplary endoscope further includes a handle 406 for manipulating the device.

An optical system according to the present teachings can be coupled to the endoscope body 402 so as to provide light for illuminating a target area. In this embodiment, the optical system is coupled to the endoscope body via a light guide adapter 406. More specifically, the light source 102, the lens 104, the tapered light pipe 108, and a portion of the light guide 106 are positioned within a housing 406a of the optical adapter 406. The light guide 106 extends from the optical coupler to the flexible element 404 with the distal ends of the light guide located in proximity of the distal end (DE) of the flexible element such that the light traveling through the light guide 106 can exit the distal end of the flexible element to illuminate a target region of interest.

Those having ordinary skill in the art will appreciate that various changes can be made to the above embodiments without departing from the scope of the invention.

What is claimed is:

1. An optical system, comprising:
    a lens having:
        an input surface configured to receive light from at least one light source;
        an output surface configured such that the light exits the lens through the output surface of the lens; and
        a peripheral surface extending between the input surface of the lens and the output surface of the lens, and configured to direct, via total internal reflection, at least a portion of light incident on the peripheral surface of the lens to:
            exit the lens through the output surface of the lens;
            converge to an output focal point; and
            diverge from the output focal point;
    a tapered light pipe having:
        an input surface that is optically coupled to the output surface of the lens and is configured to receive at least a portion of the light exiting the lens;
        an output surface configured such that at least a portion of the received light exits the tapered light pipe through the output surface of the tapered light pipe; and
        a peripheral surface extending between the input surface of the tapered light pipe and the output surface of the tapered light pipe,
    wherein:
        the tapered light pipe exhibits a decreasing cross sectional area characterized by a draft angle from the input surface of the tapered light pipe to the output surface of the tapered light pipe; and
    a light guide that is optically coupled to the tapered light pipe and is configured to receive at least a portion of the light exiting the output surface of the tapered light pipe,
    wherein:
        the output focal point of the lens is positioned so as to inhibit at least about 80% of the light diverging from the output focal point from exiting the tapered light pipe via the peripheral surface of the tapered light pipe, and
        the input surface of the tapered light pipe is flat.

2. The optical system of claim 1, wherein the output focal point is positioned within the tapered light pipe at a location selected so as to inhibit at least about 80% of the light diverging from the output focal point from exiting the tapered light pipe via the peripheral surface of the tapered light pipe.

3. The optical system of claim 1, wherein said output focal point is positioned along an optical axis of said tapered light pipe.

4. The optical system of claim 3, wherein a maximum distance $x_{max}$ of the output focal point relative to the output surface of the tapered light pipe is given by:

$$x_{max} = \frac{R_{out}}{\tan(\alpha)}$$

wherein:
    $R_{out}$ denotes a radius of the output surface of the tapered light pipe, and
    $\alpha$ denotes half of a divergence angle of the light propagating beyond the output focal point.

5. The optical system of claim 1, wherein a location of the output focal point is closer to the output surface of the tapered light pipe than to the input surface of the tapered light pipe.

6. The optical system of claim 1, wherein the output focal point is positioned at a location within the tapered light pipe such that at least about 80% of the light diverging from the output focal point exits the tapered light pipe without striking the peripheral surface of the tapered light pipe.

7. The optical system of claim 1, wherein said output focal point is positioned at a location within said tapered light pipe such that light diverging from said output focal point exhibits a divergence angle commensurate with a numerical aperture of said light guide.

8. The optical system of claim 1, wherein the draft angle is in a range of about 1 degree to about 20 degrees.

9. The optical system of claim 1, wherein said input surface of the lens comprises a cavity for receiving the light emitted by said at least one light source.

10. The optical system of claim 9, wherein at least a portion of the peripheral surface of the lens has an elliptical shape having two focal points including an input focal point positioned in the cavity and the output focal point, such that the output focal point is positioned in the tapered light pipe.

11. The optical system of claim 10, wherein at least a portion of a light-emitting surface of the light source is positioned at the input focal point.

12. An endoscope, comprising the optical system of claim 1.

13. An optical system, comprising:
    a lens having:

an input surface configured to receive light from at least one light source;

an output surface configured such that the light exits the lens through the output surface of the lens; and a peripheral surface extending between the input surface of the lens and the output surface of the lens, and configured to direct, via total internal reflection, at least a portion of light incident on the peripheral surface of the lens to:

exit the lens through the output surface of the lens;
converge to an output focal point; and
diverge from the output focal point;

a light pipe having:

an input surface that is optically coupled to the output surface of the lens and is configured to receive at least a portion of the light exiting the lens;

an output surface configured such that at least a portion of the received light exits the light pipe through the output surface of the light pipe; and a peripheral surface extending between the input surface of the light pipe and the output surface of the light pipe; and a light guide that is optically coupled to the light pipe and is configured to receive at least a portion of the light exiting the output surface of the light pipe, wherein:

the output focal point of the lens is positioned so as to inhibit at least about 80% of the light diverging from the output focal point from exiting the light pipe via the peripheral surface of the light pipe, and the input surface of the light pipe is flat.

14. The optical system of claim 13, wherein the light pipe is a tapered light pipe exhibiting a decreasing cross sectional area from the input surface of the light pipe to the output surface of the light pipe.

15. The optical system of claim 13, wherein a maximum distance $x_{max}$ of the output focal point relative to the output surface of the light pipe is given by:

$$x_{max}=R_{out}/\tan(\alpha)$$

wherein $R_{out}$ denotes a radius of the output surface of the light pipe, and $\alpha$ denotes half of a divergence angle of the light diverging from the output focal point.

16. The optical system of claim 13, wherein the output focal point is positioned along an optical axis of the light pipe.

17. The optical system of claim 13, wherein the output focal point is positioned at a location within the light pipe such that at least about 80% of the light diverging from the output focal point exits the light pipe without striking the peripheral surface of the light pipe.

18. The optical system of claim 13, wherein the output focal point is positioned within the light pipe.

19. The optical system of claim 13, wherein the output focal point is positioned at a location within the light pipe such that the light diverging from the output focal point exhibits a divergence angle commensurate with a numerical aperture of the light guide.

20. The optical system of claim 13, wherein at least a portion of the peripheral surface of the lens has an elliptical shape having two focal points including an input focal point positioned in a lens cavity configured to receive light emitted by the at least one light source and the output focal point, such that the output focal point is positioned in the light pipe.

21. The optical system of claim 20, wherein at least a portion of a light-emitting surface of the light source is positioned at the input focal point.

22. The optical system of claim 13, wherein a location of the output focal point is closer to the output surface of the light pipe than to the input surface of the light pipe.

23. An optical system, comprising:

a lens having:

an input surface configured to receive light from at least one light source;

an output surface configured such that the light exits the lens through the output surface of the lens; and a peripheral surface extending between the input surface of the lens and the output surface of the lens, and configured to direct, via total internal reflection, at least a portion of light incident on the peripheral surface of the lens to:

exit the lens through the output surface of the lens;
converge to an output focal point; and
diverge from the output focal point;

a light pipe having:

an input surface that is optically coupled to the output surface of the lens and is configured to receive at least a portion of the light exiting the lens;

an output surface configured such that at least a portion of the received light exits the light pipe through the output surface of the light pipe; and a peripheral surface extending between the input surface of the light pipe and the output surface of the light pipe; and a light guide that is optically coupled to the light pipe and is configured to receive at least a portion of the light exiting the output surface of the light pipe, wherein:

the output focal point of the lens is positioned so as to inhibit at least about 80% of the light diverging from the output focal point from exiting the light pipe via the peripheral surface of the light pipe, and a location of the output focal point is closer to the output surface of the light pipe than to the input surface of the light pipe.

\* \* \* \* \*